US012682453B2

(12) United States Patent　　　　　(10) Patent No.:　US 12,682,453 B2
Momoki　　　　　　　　　　　　　　　(45) Date of Patent:　　　Jul. 14, 2026

(54) INFORMATION PROCESSING DEVICE HAS PROCESSOR THAT OBTAINS ANALYSIS RESULTS AND DIAGNOSTIC INFORMATION REGARDING PATIENT MEDICAL IMAGE, AND NON-TRANSITORY COMPUTER-READABLE STORAGE MEDIUM

(71) Applicant: FUJIFILM Corporation, Tokyo (JP)

(72) Inventor: Yohei Momoki, Tokyo (JP)

(73) Assignee: FUJIFILM Corporation, Tokyo (JP)

( * ) Notice:　Subject to any disclaimer, the term of this patent is extended or adjusted under 35 U.S.C. 154(b) by 274 days.

(21) Appl. No.: 18/355,397

(22) Filed:　Jul. 19, 2023

(65)　　　　Prior Publication Data

US 2023/0360213 A1　　Nov. 9, 2023

Related U.S. Application Data

(63) Continuation of application No. PCT/JP2021/041617, filed on Nov. 11, 2021.

(30)　　Foreign Application Priority Data

Jan. 27, 2021　(JP) ................................ 2021-011350

(51) Int. Cl.
　　*G06T 7/00*　　　(2017.01)
　　*A61B 5/055*　　(2006.01)
　　*G16H 50/20*　　(2018.01)
　　*G06V 30/10*　　(2022.01)
(52) U.S. Cl.
　　CPC ........... *G06T 7/0012* (2013.01); *A61B 5/055* (2013.01); *G16H 50/20* (2018.01); *G06T 2207/30096* (2013.01); *G06V 30/10* (2022.01)

(58) Field of Classification Search
　　None
　　See application file for complete search history.

(56)　　　　References Cited

U.S. PATENT DOCUMENTS 8,949,171　B2 *　2/2015　Kawagishi .............. G16Z 99/00
　　　　　　　　　　　　　　　　　　706/52
10,181,098　B2　　1/2019　Vinyals et al.
10,268,671　B2　　4/2019　Kaiser et al.
2010/0280842　A1 *　11/2010　Iwase ..................... G16H 30/20
　　　　　　　　　　　　　　　　　　705/2

(Continued)

FOREIGN PATENT DOCUMENTS

JP　　　2017189237　　10/2017
JP　　　2019149005　　9/2019

(Continued)

OTHER PUBLICATIONS

"International Search Report (Form PCT/ISA/210) of PCT/JP2021/041617," mailed on Feb. 15, 2022, with English translation thereof, pp. 1-5.

(Continued)

*Primary Examiner* — Haris Sabah
(74) *Attorney, Agent, or Firm* — JCIPRNET

(57)　　　　ABSTRACT

A processor acquires one or more analysis results related to a medical image of a patient, acquires diagnostic information related to a diagnosis of the patient other than the analysis results, and generates a medical sentence related to the patient based on the analysis results and the diagnostic information.

11 Claims, 8 Drawing Sheets

<DIAGNOSTIC INFORMATION>
Nodule [MASS] → 3
Diameter [MAJOR AXIS 24 mm] → 1
Segment [LOWER RIGHT LOBE S6] → 2
<ANALYSIS RESULT>
Solid [SOLID TYPE] → 6
Lobulated+ [PRESENCE OF LOBULATED SHAPE] → 5
Airbronchogram– [ABSENCE OF AIR BRONCHOGRAM] → 9
Cavity– [ABSENCE OF CAVITY] → 8
Calcification– [ABSENCE OF CALCIFICATION] → 4
PleuralContact+ [PRESENCE OF PLEURAL CONTACT] → 6
HistoryOsteosarcoma [PRESENCE OF OSTEOSARCOMA HISTORY]

(56)          References Cited

U.S. PATENT DOCUMENTS

| | | | | |
|---|---|---|---|---|
| 2019/0267120 | A1* | 8/2019 | Hirakawa | G16H 15/00 |
| 2019/0267132 | A1* | 8/2019 | Fuchigami | G06T 11/60 |
| 2019/0279751 | A1 | 9/2019 | Nakamura et al. | |
| 2020/0160516 | A1* | 5/2020 | Fuchigami | A61B 6/032 |
| 2022/0013205 | A1 | 1/2022 | Hasegawa | |

FOREIGN PATENT DOCUMENTS

| | | |
|---|---|---|
| JP | 2019153250 | 9/2019 |
| WO | 2020202822 | 10/2020 |

OTHER PUBLICATIONS

"Written Opinion of the International Searching Authority (Form PCT/ISA/237) of PCT/JP2021/041617," mailed on Feb. 15, 2022, with English translation thereof, pp. 1-7.
"Search Report of Europe Counterpart Application", issued on Jun. 14, 2024, pp. 1-9.
"Notice of Reasons for Refusal of Japan Counterpart Application", issued on Oct. 28, 2025, with English translation thereof, pp. 1-8.

* cited by examiner

20

INFORMATION PROCESSING APPARATUS

21

INFORMATION ACQUISITION UNIT

22

ANALYSIS UNIT

22A

LEARNING MODEL

23

SENTENCE GENERATION UNIT

23A

LEARNING MODEL

24

DISPLAY CONTROL UNIT

LOCATION OF ABNORMAL SHADOW: UPPER LEFT SECTION
TYPE OF ABSORPTION VALUE: SOLID TYPE
SPICULA: +
CALCIFICATION: +
CAVITY: +
PLEURAL INVAGINATION: −

FIG. 6

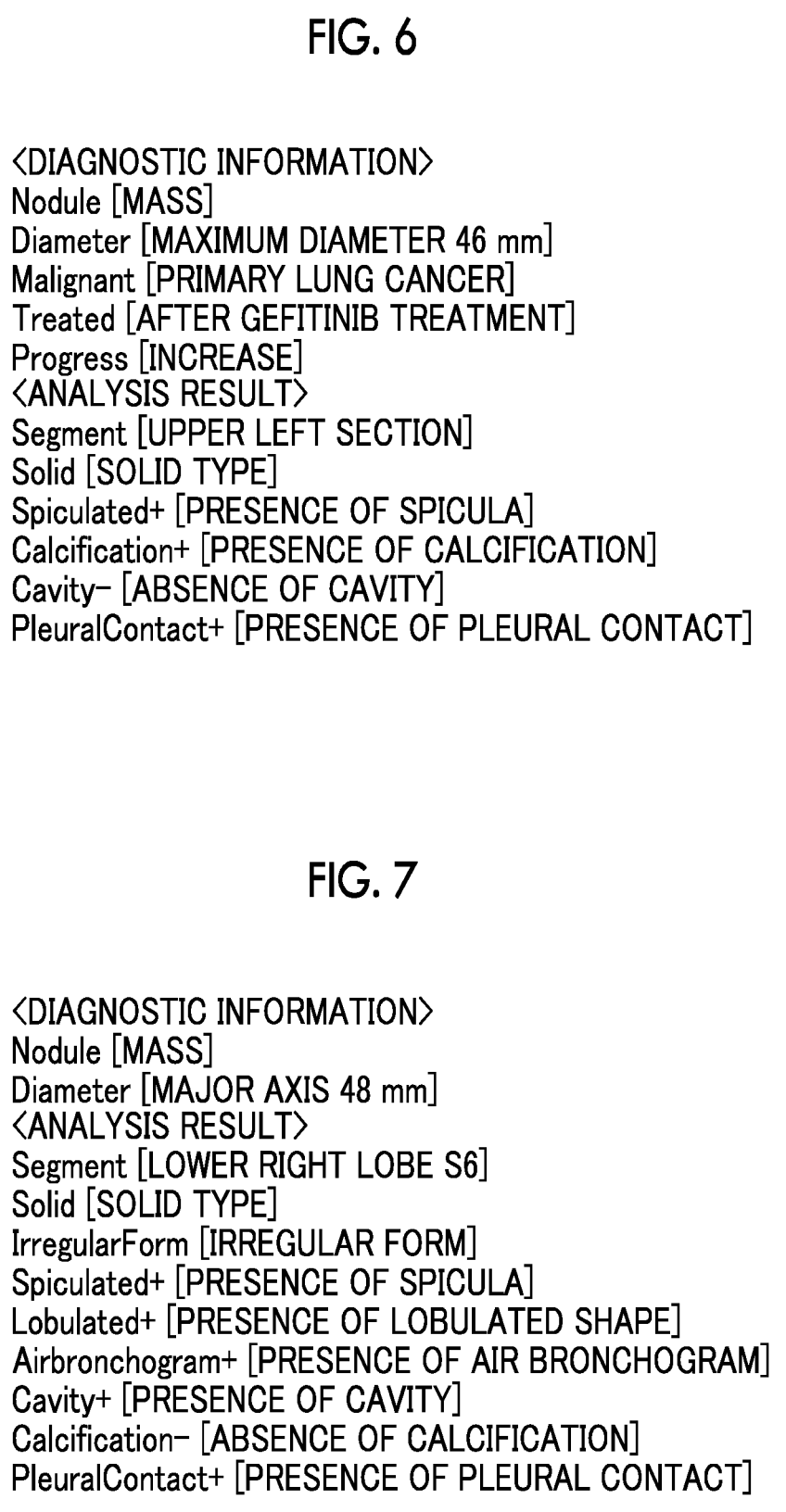

<DIAGNOSTIC INFORMATION>
Nodule [MASS]
Diameter [MAXIMUM DIAMETER 46 mm]
Malignant [PRIMARY LUNG CANCER]
Treated [AFTER GEFITINIB TREATMENT]
Progress [INCREASE]
<ANALYSIS RESULT>
Segment [UPPER LEFT SECTION]
Solid [SOLID TYPE]
Spiculated+ [PRESENCE OF SPICULA]
Calcification+ [PRESENCE OF CALCIFICATION]
Cavity- [ABSENCE OF CAVITY]
PleuralContact+ [PRESENCE OF PLEURAL CONTACT]

FIG. 7

<DIAGNOSTIC INFORMATION>
Nodule [MASS]
Diameter [MAJOR AXIS 48 mm]
<ANALYSIS RESULT>
Segment [LOWER RIGHT LOBE S6]
Solid [SOLID TYPE]
IrregularForm [IRREGULAR FORM]
Spiculated+ [PRESENCE OF SPICULA]
Lobulated+ [PRESENCE OF LOBULATED SHAPE]
Airbronchogram+ [PRESENCE OF AIR BRONCHOGRAM]
Cavity+ [PRESENCE OF CAVITY]
Calcification- [ABSENCE OF CALCIFICATION]
PleuralContact+ [PRESENCE OF PLEURAL CONTACT]

FIG. 8

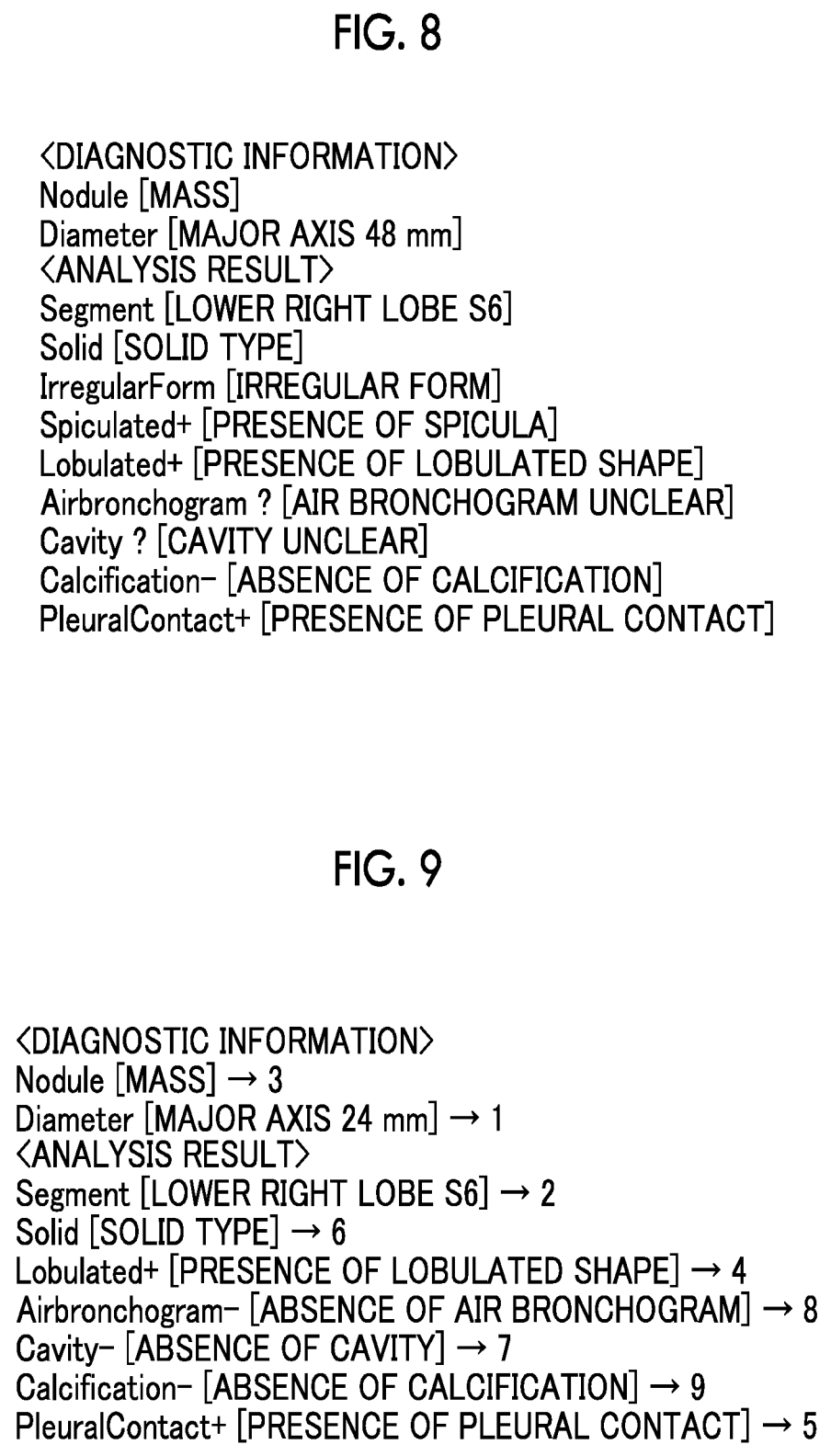

<DIAGNOSTIC INFORMATION>
Nodule [MASS]
Diameter [MAJOR AXIS 48 mm]
<ANALYSIS RESULT>
Segment [LOWER RIGHT LOBE S6]
Solid [SOLID TYPE]
IrregularForm [IRREGULAR FORM]
Spiculated+ [PRESENCE OF SPICULA]
Lobulated+ [PRESENCE OF LOBULATED SHAPE]
Airbronchogram ? [AIR BRONCHOGRAM UNCLEAR]
Cavity ? [CAVITY UNCLEAR]
Calcification− [ABSENCE OF CALCIFICATION]
PleuralContact+ [PRESENCE OF PLEURAL CONTACT]

FIG. 9

<DIAGNOSTIC INFORMATION>
Nodule [MASS] → 3
Diameter [MAJOR AXIS 24 mm] → 1
<ANALYSIS RESULT>
Segment [LOWER RIGHT LOBE S6] → 2
Solid [SOLID TYPE] → 6
Lobulated+ [PRESENCE OF LOBULATED SHAPE] → 4
Airbronchogram− [ABSENCE OF AIR BRONCHOGRAM] → 8
Cavity− [ABSENCE OF CAVITY] → 7
Calcification− [ABSENCE OF CALCIFICATION] → 9
PleuralContact+ [PRESENCE OF PLEURAL CONTACT] → 5

FIG. 10

<DIAGNOSTIC INFORMATION>
Nodule [MASS] → 3
Diameter [MAJOR AXIS 24 mm] → 1
Segment [LOWER RIGHT LOBE S6] → 2
<ANALYSIS RESULT>
Solid [SOLID TYPE] → 6
Lobulated+ [PRESENCE OF LOBULATED SHAPE] → 5
Airbronchogram− [ABSENCE OF AIR BRONCHOGRAM] → 9
Cavity− [ABSENCE OF CAVITY] → 8
Calcification− [ABSENCE OF CALCIFICATION] → 4
PleuralContact+ [PRESENCE OF PLEURAL CONTACT] → 6
HistoryOsteosarcoma [PRESENCE OF OSTEOSARCOMA HISTORY]

FIG. 11

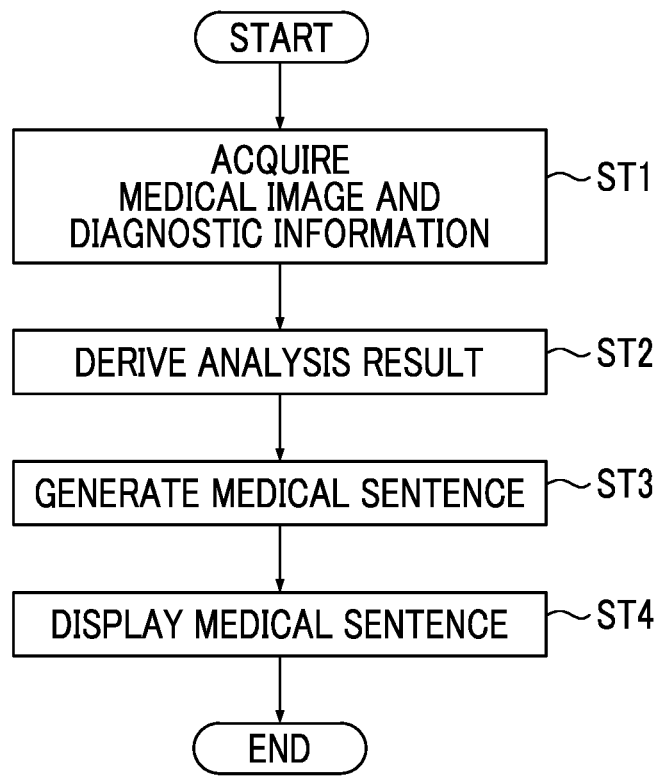

| | ANALYSIS RESULT | | | | | | | | | |
|---|---|---|---|---|---|---|---|---|---|---|
| | ABSORPTION VALUE | | EDGE | | INTERNAL PROPERTY | | | | PERIPHERY | |
| | SOLID TYPE | FROSTED GLASS TYPE | PRESENCE OF SPICULA | ABSENCE OF SPICULA | PRESENCE OF CAVITY | ABSENCE OF CAVITY | PRESENCE OF CALCIFICATION | ABSENCE OF CALCIFICATION | PRESENCE OF PLEURAL INVAGINATION | ABSENCE OF PLEURAL INVAGINATION |
| DIAMETER (≪ 5 mm) | × | × | × | × | × | × | ○ | × | × | × |
| DIAMETER (≪ 10 mm) | ○ | ○ | ○ | ○ | ○ | × | ○ | ○ | ○ | × |
| DEFINITIVE DIAGNOSIS OF MALIGNITY | × | × | × | × | × | × | × | × | × | × |

INFORMATION PROCESSING DEVICE HAS PROCESSOR THAT OBTAINS ANALYSIS RESULTS AND DIAGNOSTIC INFORMATION REGARDING PATIENT MEDICAL IMAGE, AND NON-TRANSITORY COMPUTER-READABLE STORAGE MEDIUM

CROSS-REFERENCE TO RELATED APPLICATIONS

The present application is a Continuation of PCT International Application No. PCT/JP2021/041617, filed on Nov. 11, 2021, which claims priority to Japanese Patent Application No. 2021-011350, filed on Jan. 27, 2021. Each application above is hereby expressly incorporated by reference, in its entirety, into the present application.

BACKGROUND

Technical Field

The present disclosure relates to an information processing apparatus, method, and program.

Related Art

In recent years, advances in medical apparatuses such as computed tomography (CT) apparatuses and magnetic resonance imaging (MRI) apparatuses have enabled image diagnosis using high-resolution medical images with higher quality. In particular, since a region of a lesion can be accurately specified by image diagnosis using a CT image, an MRI image, and the like, appropriate treatment is being performed based on the specified result.

In addition, a medical image is analyzed by computer-aided diagnosis (CAD) using a learning model in which learning is performed by deep learning or the like, and properties such as a shape, a density, a position, and a size of an abnormal shadow such as a lesion included in the medical image are detected. An analysis result obtained in this manner is stored in a database in association with examination information such as a name, a gender, and an age of a patient, and an imaging apparatus which has acquired the medical image. The medical image and the analysis result are transmitted to a terminal of a radiologist who interprets the medical image. The radiologist interprets the medical image with reference to the transmitted medical image and the analysis result on his/her own interpretation terminal, and creates an interpretation report.

On the other hand, the number of medical images to be interpreted is increasing with the improvement in the performance of the CT apparatus and the MRI apparatus described above. Therefore, in order to reduce a burden on the radiologist for interpretation work, various methods have been proposed for supporting creation of a medical document such as an interpretation report. For example, a method for generating a sentence to be described in an interpretation report based on a keyword representing findings based on a medical image input by a radiologist and information representing a property of an abnormal shadow included in an analysis result of the medical image has been disclosed (see JP2019-153250A). In the method described in JP2019-153250A, the medical sentence to be described in the interpretation report is generated using a learning model such as a recurrent neural network in which machine learning is performed so as to generate the medical sentence from characters representing an input property.

In a case where image diagnosis is performed, other examinations such as a blood examination are often performed together with acquisition of an image of a patient. Further, not only one type of an image such as a CT image but also a plurality of types of images including an MRI image and the like may be used for image diagnosis. Therefore, as in the method described in JP2019-153250A, in a case where only the analysis result of the medical image and the findings input by the radiologist are used, the sentence generated by the learning model will not necessarily be a medical sentence having contents accurately representing a situation of the patient.

SUMMARY OF THE INVENTION

The present disclosure has been made in view of the above circumstances, and an object of the present disclosure is to enable generation of a medical sentence having contents accurately representing a situation of a patient.

An information processing apparatus according to an aspect of the present disclosure comprises at least one processor, in which the processor is configured to: acquire one or more analysis results related to a medical image of a patient; acquire diagnostic information related to a diagnosis of the patient other than the analysis results, and generate a medical sentence related to the patient based on the analysis results and the diagnostic information.

In the information processing apparatus according to the aspect of the present disclosure, the processor may select the analysis result based on the diagnostic information; and generate a medical sentence including the selected analysis result.

In the information processing apparatus according to the aspect of the present disclosure, the processor may generate the medical sentence including the analysis result with a priority corresponding to the diagnostic information.

In the information processing apparatus according to the aspect of the present disclosure, the processor may generate the medical sentence including the diagnostic information and the analysis result.

In the information processing apparatus according to the aspect of the present disclosure, the diagnostic information may include first information confirmed for a lesion included in the medical image.

In this case, the first information may include at least one of a measurement result of the lesion, a definitive diagnosis result for the lesion, or a history of the patient.

In the information processing apparatus according to the aspect of the present disclosure, the diagnostic information may include confirmed second information other than information related to a lesion included in the medical image.

In this case, the second information may include at least one of a purpose of an examination in which the medical image is acquired or an image condition related to the medical image.

In the information processing apparatus according to the aspect of the present disclosure, the diagnostic information may include third information representing a determination result for the medical image by a radiologist.

In this case, the third information may include at least one of an unconfirmed diagnosis result related to the medical image, a relevance between a lesion included in the medical image and a tissue other than the lesion, or a selection result of the analysis result by the radiologist.

In the information processing apparatus according to the aspect of the present disclosure, the diagnostic information may include fourth information representing an examination result performed on the patient.

In this case, the fourth information may include at least one of an examination result of a diagnostic apparatus different from an imaging apparatus that acquires the medical image of the patient, an analysis result of a medical image of a type different from the medical image, or an examination result of biological information of the patient.

An information processing method according to another aspect of the present disclosure comprises acquiring one or more analysis results related to a medical image of a patient; acquires diagnostic information related to a diagnosis of the patient other than the analysis results; and generates a medical sentence related to the patient based on the analysis results and the diagnostic information.

A program for causing a computer to execute the information processing method according to the other aspect of the present disclosure may be provided.

According to the present disclosure, it is possible to generate a medical sentence having contents accurately representing a status of a patient.

BRIEF DESCRIPTION OF THE DRAWINGS

FIG. 6 is a diagram showing an example of diagnostic information and the analysis result.

FIG. 7 is a diagram showing an example of a label of the diagnostic information.

FIG. 8 is a diagram showing an example of the label of the diagnostic information.

FIG. 9 is a diagram showing an example of the label of the diagnostic information.

FIG. 10 is a diagram showing an example of the label of the diagnostic information.

FIG. 11 is a flowchart showing a process performed in the first embodiment.

FIG. 13 is a diagram showing an example of a table in which a rule for selecting analysis information is defined in the second embodiment.

DETAILED DESCRIPTION

Hereinafter, embodiments of the present disclosure will be described with reference to the drawings. First, a configuration of a medical information system 1 to which an information processing apparatus according to a first embodiment is applied will be described.

Figures 1, 2:
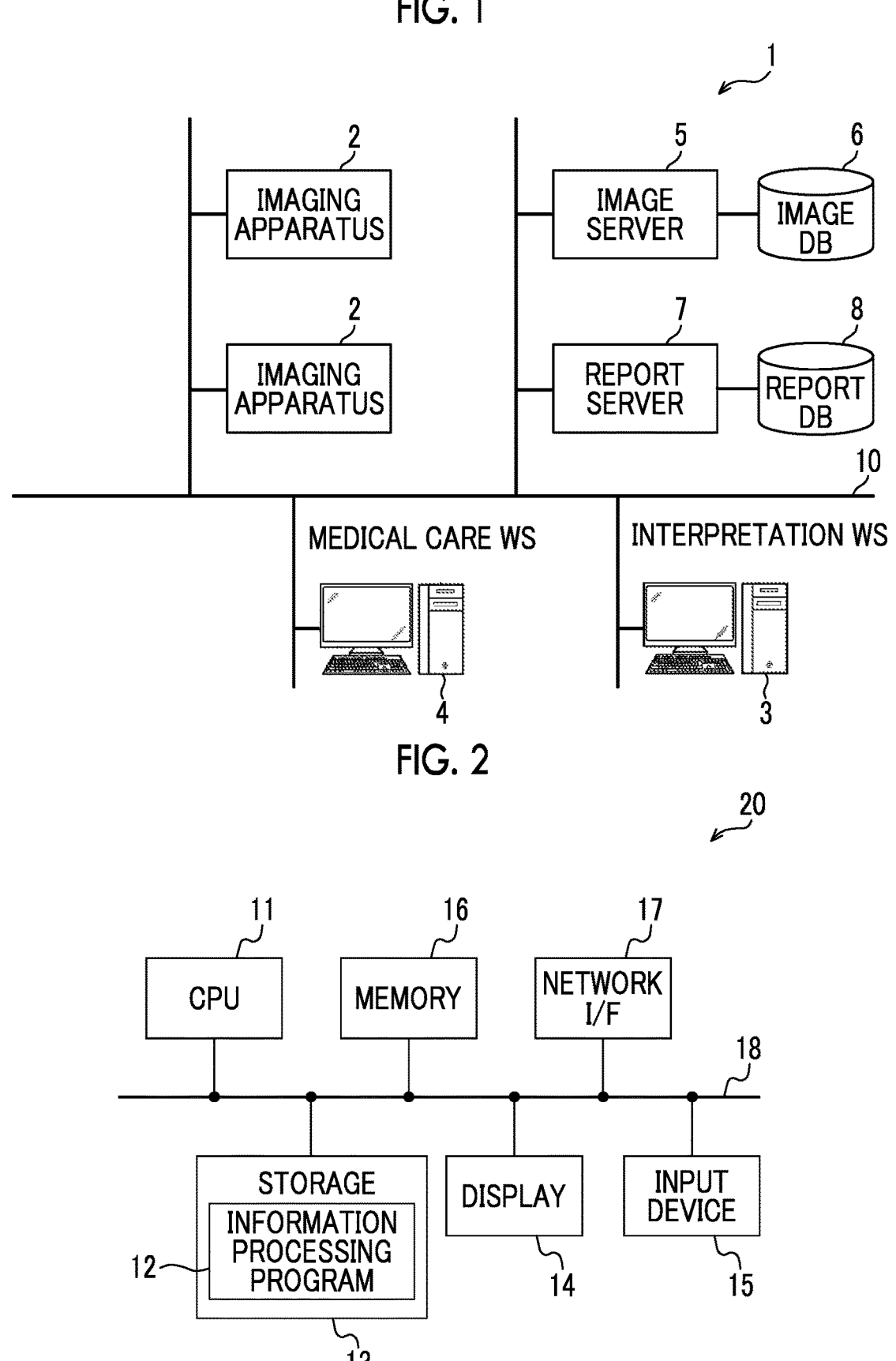
FIG. 1 is a diagram showing an example of a schematic configuration of a medical information system to which an information processing apparatus according to a first embodiment is applied.
FIG. 2 is a block diagram showing an example of a hardware configuration of the information processing apparatus according to the first embodiment.

FIG. 1 is a diagram showing a schematic configuration of a medical information system 1. A medical information system 1 shown in FIG. 1 is a system for performing, based on an examination order from a doctor in a clinical department using a known ordering system, imaging of an examination target part of a patient which is a subject, storage of a medical image acquired by imaging, interpretation of the medical image and creation of an interpretation report by a radiologist, and browsing of the interpretation report and detailed observation of a medical image to be interpreted by the doctor in the clinical department of a request source.

As shown in FIG. 1, the medical information system 1 is configured by connecting a plurality of imaging apparatuses 2, a plurality of interpretation workstations (WS) 3 that are interpretation terminals, a medical care WS 4, an image server 5, an image database (DB) 6, a report server 7, and a report DB 8 through a wired or wireless network 10 in a communicable state.

Each apparatus is a computer on which an application program for causing each apparatus to function as a component of the medical information system 1 is installed. The application program is recorded in a recording medium such as a digital versatile disc (DVD) and a compact disc read only memory (CD-ROM), is distributed, and is installed on the computer from the recording medium. Alternatively, the application program is stored in a storage device of a server computer connected to the network 10 or in a network storage in a state of being accessible from the outside, and is downloaded to and installed on the computer in response to a request.

The imaging apparatus 2 is an apparatus (modality) that generates a medical image showing a diagnosis target part of the patient by imaging the diagnosis target part of the patient. Specifically, examples of the imaging apparatus include a simple X-ray imaging apparatus, a CT apparatus, an MRI apparatus, a positron emission tomography (PET) apparatus, and the like. The medical image generated by the imaging apparatus 2 is transmitted to the image server 5 and stored in the image DB 6.

The interpretation WS 3 is a computer used by, for example, a radiologist of a radiology department to interpret a medical image and to create an interpretation report, and includes an information processing apparatus 20 (details will be described below) according to the first embodiment. In the interpretation WS 3, a request for browsing the medical image to the image server 5, various types of image processing on the medical image received from the image server 5, display of the medical image, and input reception of a finding sentence regarding the medical image are performed. In the interpretation WS 3, analysis processing on the medical image, a support for creation of an interpretation report based on an analysis result, a registration request and a browsing request for the interpretation report to the report server 7, and display of the interpretation report received from the report server 7 are performed. The above processes are performed by executing a software program for each process in the interpretation WS 3.

The medical care WS 4 is a computer used, for example, by a doctor in a clinical department for detailed observation of an image, browsing of an interpretation report, creation of an electronic medical record, and the like, and includes a processing device, a display apparatus such as a display, and an input device such as a keyboard and a mouse. In the medical care WS 4, a browsing request for the image to the image server 5, display of the image received from the image server 5, a browsing request for the interpretation report to the report server 7, and display of the interpretation report received from the report server 7 are performed. The above processes are performed by the medical care WS 4 executing a software program for each process.

The image server 5 is a general-purpose computer on which a software program for providing a function of a database management system (DBMS) is installed. Further, the image server 5 comprises a storage in which an image DB 6 is configured. The storage may be a hard disk device connected to the image server 5 via a data bus, or may be a disk device connected to a network attached storage (NAS) or a storage area network (SAN) connected to the network 10. In a case where the image server 5 receives a registration request for the medical image from the imaging apparatus 2, the image server 5 prepares the medical image in a database format and registers the medical image in the image DB 6.

In the present embodiment, the image server 5 stores diagnostic information related to diagnosis of a patient. The diagnostic information will be described later.

Image data of the medical image acquired by the imaging apparatus 2 and accessory information are registered in the image DB 6. The accessory information includes, for example, an image identification (ID) for identifying each medical image, a patient ID for identifying a patient, an examination ID for identifying an examination, a unique identification (UID) assigned to each medical image, an examination date and examination time at which the medical image is generated, a type of an imaging apparatus used in an examination for acquiring the medical image, patient information such as a name, age, and gender of a patient, an examination part (imaging part), imaging information (imaging protocol, an imaging sequence, an imaging method, imaging conditions, use of a contrast medium, and the like), and information such as a series number or collection number in a case where a plurality of medical images are acquired in one examination.

In a case where a browsing request from the interpretation WS 3 and the medical care WS 4 is received through the network 10, the image server 5 searches for a medical image registered in the image DB 6 and transmits the searched for medical image to the interpretation WS 3 and the medical care WS 4 that are request sources.

A software program that provides a function of a database management system to a general-purpose computer is incorporated into the report server 7. In a case where the report server 7 receives the registration request for the interpretation report from the interpretation WS 3, the report server 7 prepares the interpretation report in a database format and registers the interpretation report in the report DB 8.

An interpretation report including a finding sentence created by the radiologist using the interpretation WS 3 is registered in the report DB 8. The interpretation report may include, for example, information such as a medical image to be interpreted, an image ID for identifying the medical image, a radiologist ID for identifying the radiologist who has performed the interpretation, a lesion name, positional information of the lesion, and a property of the lesion.

In a case where the report server 7 receives the browsing request for the interpretation report from the interpretation WS 3 and the medical care WS 4 through the network 10, the report server 7 searches for the interpretation report registered in the report DB 8 and transmits the searched for interpretation report to the interpretation WS 3 and the medical care WS 4 that are request sources.

The network 10 is a wired or wireless local area network that connects various apparatuses in a hospital to each other. In a case where the interpretation WS 3 is installed in another hospital or clinic, the network 10 may be configured to connect local area networks of respective hospitals to each other through the internet or a dedicated line.

Next, the information processing apparatus 20 according to the first embodiment will be described. First, a hardware configuration of the information processing apparatus 20 according to the first embodiment will be described with reference to FIG. 2. As shown in FIG. 2, the information processing apparatus 20 includes a central processing unit (CPU) 11, a non-volatile storage 13, and a memory 16 as a temporary storage area. The information processing apparatus 20 includes a display 14 such as a liquid crystal display, an input device 15 including a pointing device such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, or the like. An information processing program 12 is stored in the storage 13 as a storage medium. The CPU 11 reads out the information processing program 12 from the storage 13, loads the information processing program 12 in the memory 16, and executes the loaded information processing program 12.

Figures 3, 4:
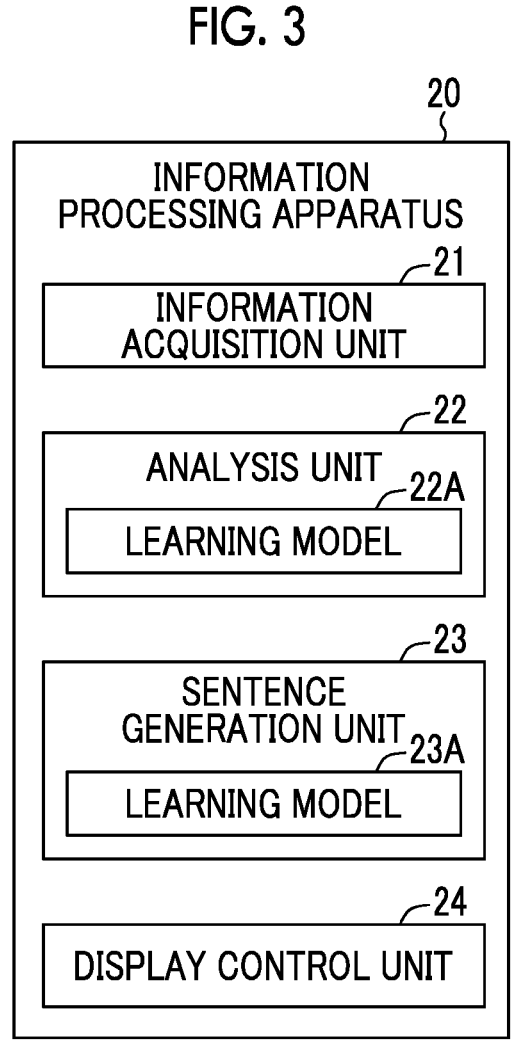
FIG. 3 is a block diagram showing an example of a functional configuration of the information processing apparatus according to the first embodiment.
FIG. 4 is a diagram showing an example of an analysis result.

Next, a functional configuration of the information processing apparatus according to the first embodiment will be described. FIG. 3 is a diagram showing the functional configuration of the information processing apparatus according to the first embodiment. As shown in FIG. 3, the information processing apparatus 20 comprises an information acquisition unit 21, an analysis unit 22, a sentence generation unit 23, and a display control unit 24. As the CPU 11 executes the information processing program 12, the CPU 11 functions as the information acquisition unit 21, the analysis unit 22, the sentence generation unit 23, and the display control unit 24.

The information acquisition unit 21 acquires a medical image G0 as an example of an image from the image server 5 through the network I/F 17. In the first embodiment, as an example, a CT image of the lung is used as the medical image G0. Further, the information acquisition unit 21 acquires diagnostic information related to diagnosis of a patient from which the medical image G0 is acquired, from the image server 5 through the network I/F 17. The diagnostic information will be described later.

The analysis unit 22 derives an analysis result of the medical image G0 by analyzing the medical image G0. For this purpose, the analysis unit 22 has a learning model 22A in which machine learning is performed so as to detect an abnormal shadow such as a lesion included in the medical image G0 and to discriminate a property for the detected abnormal shadow for each of a plurality of predetermined property items.

Here, examples of the property items specified for the abnormal shadow of the lung include a location of the abnormal shadow, a type of an absorption value (solid type and frosted glass type), the presence or absence of a spicula, the presence or absence of calcification, the presence or absence of a cavity, the presence or absence of a pleural invagination, the presence or absence of a pleural contact, and the presence or absence of a pleural infiltration. The property items are not limited to the above examples.

In the first embodiment, the learning model 22A consists of a convolutional neural network in which machine learning is performed by deep learning or the like using training data so as to discriminate the property of the abnormal shadow in the medical image.

The learning model 22A is constructed by, for example, machine learning using a combination of a medical image including an abnormal shadow and a property item representing a property of the abnormal shadow as training data. In a case where a medical image is input, the learning model 22A outputs a property score derived for each property item in the abnormal shadow included in the medical image. The property score is a score indicating a prominence of the property for each property item. The property score takes a value of, for example, 0 or more and 1 or less, and the larger the value of the property score is, the more remarkable the property is.

For example, in a case where the property score for "presence or absence of a spicula" which is one of the property items of the abnormal shadow is equal to or greater than a predetermined threshold value (for example, 0.5), the property for "presence or absence of a spicula" of the abnormal shadow specifies "presence of a spicula (positive)", and in a case where the property score for "presence or absence of a spicula" is less than the threshold value, the property for the presence or absence of a spicula of the abnormal shadow specifies "absence of a spicula (negative)". The threshold value of 0.5 used for the property determination is merely an example, and is set to an appropriate value for each property item. In a case where the property score is near the threshold value (for example, 0.4 or more and 0.6 or less), a false positive may be specified.

FIG. 4 is a diagram showing an example of an analysis result derived by the analysis unit 22. As shown in FIG. 4, the property information specified by the analysis unit 22 includes the property items of a location of the abnormal shadow, a type of an absorption value, a spicula, a calcification, a cavity, and a pleural invagination, and the properties for the property items are "upper left section", "solid type", "presence of a spicula", "presence of calcification", "presence of a cavity", and "absence of a pleural invagination". In FIG. 4, "+" is given in a case of "presence", that is, positive, and "−" is given in a case of "absence", that is, negative.

As the learning model 22A, in addition to the convolutional neural network, for example, any learning model such as a support vector machine (SVM) can be used.

Further, a learning model for detecting an abnormal shadow from the medical image G0 and a learning model for discriminating a property of the abnormal shadow may be separately constructed.

The sentence generation unit 23 generates a medical sentence related to the patient based on the analysis result derived by the analysis unit 22 and the diagnostic information acquired by the information acquisition unit 21. In the present embodiment, the sentence generation unit 23 consists of a learning model 23A constructed by machine learning so as to generate a finding sentence to be described in an interpretation report as a medical sentence from input information. As the learning model 23A, for example, a neural network such as a recurrent neural network described in U.S. Pat. Nos. 10,181,098B or 10,268,671B can be used. In the present embodiment, the learning model 23A is constructed by training the recurrent neural network by supervised learning. The training data used in this case is data in which combinations of various analysis results and various types of diagnostic information are associated with various training sentences to be generated from the analysis results and the diagnostic information.

Figure 5:
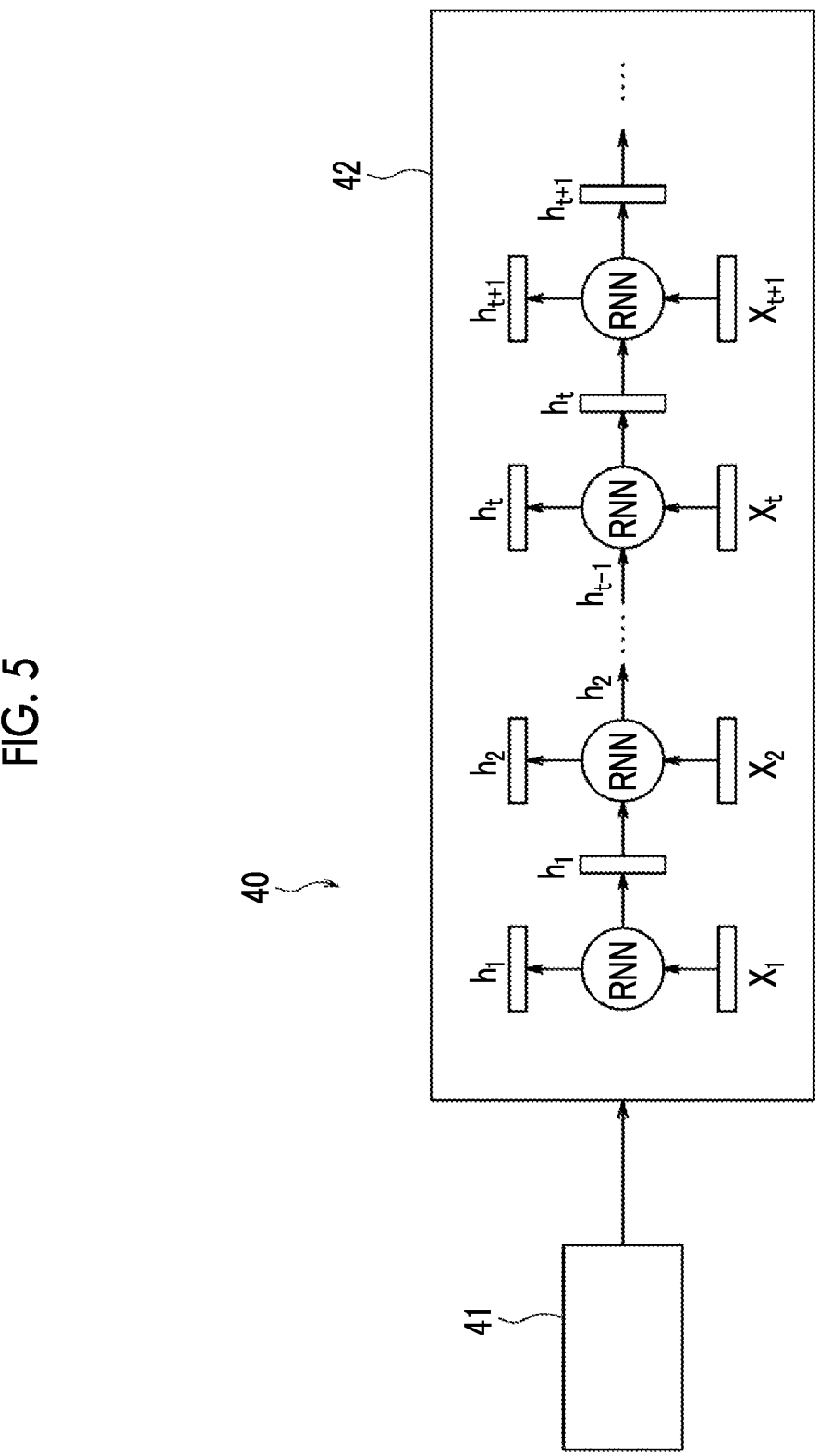
FIG. 5 is a diagram schematically showing a recurrent neural network.

FIG. 5 is a diagram schematically showing a recurrent neural network. As shown in FIG. 5, the recurrent neural network 40 consists of an encoder 41 and a decoder 42. Labels of the analysis result derived by the analysis unit 22 and the diagnostic information are input to the encoder 41. The 1-hot expressions of the labels of the analysis result and the diagnostic information are input to the encoder 41. In the 1-hot expression, each label is represented by a vector having one component of 1 and the remaining components of 0. For example, in a case where the 1-hot expression is a vector consisting of three elements, (1, 0, 0), (0, 1, 0), and (0, 0, 1) respectively represent three different labels.

The encoder 41 transforms the 1-hot expression of each label by an embedding matrix to derive a vector representation of each label. Each element of the embedding matrix is a learning parameter. The learning parameter is determined by machine learning of the recurrent neural network 40.

The decoder 42 is configured by connecting a plurality of networks consisting of an input layer, an intermediate layer, and an output layer. In each network, a vector representation xt output from the encoder 41 and an output ht of a network in a previous stage are input. In the intermediate layer, calculation shown in Expression (1) below is performed. In Expression (1), Wh, Wx, and b are learning parameters and are determined by learning. tanh is an activation function. The activation function is not limited to tanh, and a sigmoid function or the like may be used.

$$ht = \tanh(ht-1 \cdot Wh + xt \cdot Wx + b) \tag{1}$$

Here, it is assumed that the analysis result of the training data and the diagnostic information are "under left lung pleura", "4.2 cm", "spicula+", and "mass". Since "under left lung pleura" is a term representing a location in the lung, a label representing the location is given. Since "4.2 cm" is a size of a diameter, a label indicating the size is given. "spicula+" is given a label indicating that the spicula is positive, and "mass" is given a label indicating a medically small mass. These labels are input to the encoder 41, and a vector representation of each label is output.

In the decoder 42, the output of the previous stage and the vector representation are input to the input layer of each neural network, and a finding sentence "[small mass] with [size] diameter having [spicula] is recognized at [location]" is output. The sentence generation unit 23 embeds information on the analysis result and the diagnostic information into the label included in the finding sentence output from the learning model 23A, to generate a sentence "a mass having a diameter of 4.2 cm with a spicula is recognized under the left lung pleura".

Here, the diagnostic information used in the present embodiment will be described. The diagnostic information is information relating to diagnosis of the patient other than the analysis result derived by the analysis unit 22. Specifically, examples of the diagnostic information include information (referred to as first information D1) confirmed regarding a lesion included in the medical image, confirmed information (referred to as second information D2) other than the information related to the lesion included in the medical image, information (referred to as third information D3) representing a determination result for the medical image by a radiologist, and information (referred to as fourth information D4) representing an examination result performed on the patient.

The first information D1 confirmed for the lesion included in the medical image G0 includes, for example, measurement information such as the size (vertical and horizontal lengths or an area) of the lesion included in the medical image G0, a definitive diagnosis result for the lesion, a history of the patient from whom the medical image G0 has been acquired, and contents of treatment performed on the patient. Regarding the size of the lesion, information representing a change over time from the size of the lesion included in the medical image acquired in the past for the same patient can be used as the first information D1. The information representing the change is information representing whether the size of the lesion is increasing, decreasing, or not changing. The definitive diagnosis result regarding the lesion is a diagnosis result confirmed by a doctor, such as whether the lesion is cancer or a benign tumor. The history of the patient is a history of diseases suffered in the past by the patient from whom the medical image G0 has been acquired. Examples of the contents of treatment performed on the patient include contents of surgery performed on the patient, a type of medicine used, an amount of medicine, a medication period, and the like.

Regarding the generation of the finding sentence using the first information D1, the diagnostic information may be directly included in the finding sentence (for example, there is a history of primary lung cancer or colorectal cancer with a major axis of 10 mm). In this case, the learning model 23A may be constructed by training the neural network using training data that includes labels of a size, definitive diagnosis of malignity, and a history as the first information D1 in the diagnostic information and includes a training sentence in which the labels are described.

In addition, for example, since it is difficult to evaluate an internal property other than calcification in a nodule having a major axis less than 10 mm, a finding sentence may be generated so as not to include internal negative findings (an air bronchogram, a cavity, fat, and the like) as the analysis result. In this case, the learning model 23A may be constructed by training the recurrent neural network 40 using training data that includes a label of, for example, the size as the first information D1 in the diagnostic information, includes labels of "nodule, air bronchogram–, and cavity–" in the analysis result, and includes a training sentence that does not include descriptions of the labels of the air bronchogram and the cavity among the labels.

Further, in a case where primary lung cancer is confirmed as the diagnosis result, a change (increase or decrease) in size over time is more important than pictorial properties (presence of a spicula or the like). Therefore, in the finding sentence, only a change in size over time may be described without describing an analysis result representing properties, or an analysis result inconsistent with the definitive diagnosis (for example, a finding suggesting benignity in a case where there is a definitive diagnosis of primary lung cancer) may not be described. In this case, the learning model 23A may be constructed by training the recurrent neural network 40 using training data that includes a label of definitive diagnosis of malignity such as primary lung cancer and a label of "increase" as the first information D1 in the diagnostic information, includes a label of a positive property item as the analysis result, and includes a training sentence that includes a description of the label of increase of the definitive diagnosis of malignity but does not include a description of the label of a positive property item among the labels.

The confirmed second information D2 other than the information related to the lesion included in the medical image G0 is information not related to the lesion regarding the medical image G0, and specific examples thereof include an examination purpose for acquiring the medical image G0 and an image condition in a case of acquiring the medical image G0. The acquisition of the medical image G0 is performed as a part of an examination for determining a state of a patient, and has various examination purposes such as a thorough examination or a follow-up observation. In a case where the medical image G0 is acquired, various conditions (a window level, a window width, and a slice interval) are prepared in order to make it easy to see a target organ in various modalities. The image condition is a condition in a case of generating the medical image G0 such as the window level, the window width, and the slice interval.

Regarding the generation of the finding sentence using the second information D2, the content to be described in the finding sentence varies depending on whether the examination purpose is the thorough examination or the follow-up observation. For example, the finding sentence may be generated such that detailed contents are described in the finding sentence in a case of the thorough examination, and a change (increase or decrease) in size over time is described in a case of the follow-up observation. In this case, the learning model 23A may be constructed by training the recurrent neural network 40 using, for example, training data that includes a label indicating that the examination purpose is a thorough examination as the second information D2 in the diagnostic information and includes a training sentence in which labels of all property items included in the analysis result are described, or training data that includes a label indicating that the examination purpose is a follow-up observation as the second information D2 in the diagnostic information and includes a training sentence in which only a label of a change in size is described among property labels included in the analysis result.

In addition, in a case where a slice thickness of a CT image is 5 mm, pixel values are averaged due to a partial volume effect to decrease a contrast, which makes it difficult to evaluate internal properties and edge properties. In such a case, in a case where a finding sentence with an assertive ending is generated, a creator feels uncomfortable with the finding sentence. For this reason, a finding sentence may be generated such that an analysis result which is difficult to evaluate may or may not be described according to the image condition, or described in such a way as to decrease or increase a certainty factor (change the ending from "recognized" to "suspected"), or described in a blurred or asserted expression (a frosted glass nodule is set as a light nodule, and a nodule is set as a density increased region). In this case, the learning model 23A may be constructed by training the recurrent neural network 40 using training data that includes a label indicating that a slice thickness of a CT image is 5 mm as the second information D2 in the diagnostic information, includes a label of a positive property item among labels of property items included in the analysis result, and includes a training sentence in which "~ is suspected" rather than "~ is recognized" is described at the ending of the label of the positive property item.

The third information D3 representing the determination result for the medical image by the radiologist is information representing an interpretation result for the lesion included in the medical image G0 by the radiologist who interprets the medical image G0. Specifically, examples thereof include an unconfirmed diagnosis result for the medical image G0, relevance between a lesion and a tissue other than the lesion, and a selection result of the radiologist for a plurality of analysis results.

Regarding the generation of the finding sentence using the third information D3, in a case where the third information D3 is the unconfirmed diagnosis result or the relevance between a lesion and a tissue other than the lesion, a finding sentence may be generated such that the third information D3 is directly included in the finding sentence. For example, a finding sentence with such a description that primary lung cancer is suspected, mediastinal invasion is suspected, or intrapulmonary metastasis is suspected may be generated. In this case, the learning model 23A may be constructed by training the recurrent neural network 40 using training data that includes, for example, a label indicating that "mediastinal invasion is suspected" as the third information D3 in the diagnostic information and includes a training sentence in which the label indicating that "mediastinal invasion is suspected" is described.

In addition, regarding the selection result of the radiologist for a plurality of analysis results, a finding sentence including only the property item selected by the radiologist may be generated. The property item not selected by the radiologist may not be described in the finding sentence, but the finding sentence may be generated in such a way as to lower a certainty factor, lower importance, or blur the description.

Examples of the fourth information 4 representing the examination result performed on the patient include an interpretation result for a medical image acquired by an imaging apparatus different from the imaging apparatus that acquires the medical image G0 and an examination result other than the examination using the image such as a blood examination.

Regarding the generation of a finding sentence using the fourth information D4, discrimination of tuberculoma, which is one of pulmonary diseases, is performed not only by image diagnosis but also in combination with blood examination. Therefore, diagnostic information such as a blood examination result may be directly described in a finding sentence. For example, in a case where the blood examination result is "negative quantiferon" and information on a symptom suspected based on the blood examination result is "nontuberculous mycobacteriosis", a finding sentence such as "nontuberculous mycobacteriosis is suspected due to negative quantiferon" may be described. In this case, the learning model 23A may be constructed by training the recurrent neural network 40 using training data that includes, for example, a label of "blood examination" and a label of a suspected symptom as the fourth information D4 in the diagnostic information and includes a training sentence in which these labels are described. In this case, the learning model 23A may be constructed so as to generate a finding sentence including a label of a property item included in the analysis result, or the learning model 23A may be constructed so as to generate a finding sentence not including the label of the property item.

In addition, even in a case where an examination result and an image analysis result obtained by using another diagnostic apparatus such as a contrast CT apparatus or a PET-CT apparatus other than the CT apparatus are used as diagnostic information, the diagnostic information may be similarly described in the finding sentence. For example, in a case where the examination result is "FDG accumulation in mPET is low" and the information on the symptom suspected based on the examination result is "round atelectasis or organizing pneumonia", a finding sentence such as "FDG accumulation in mPET is low and round atelectasis or organizing pneumonia is suspected" may be described. Further, the analysis result related to the diagnostic information may be described in the finding sentence, and the analysis result not related to the patient information may not be described in the finding sentence. Further, depending on whether or not the analysis result is related to the fourth information D4, the finding sentence may be generated such that the analysis result related to the fourth information D4 may or may not be described in the finding sentence, or described in such a way as to decrease or increase a certainty factor, decrease or increase importance, or blur or assert.

Hereinafter, examples of a combination of the diagnostic information and the analysis result and a finding sentence generated by the sentence generation unit 23 will be described. FIG. 6 is a diagram showing an example of the diagnostic information and the analysis result. The diagnostic information shown in FIG. 6 is the first information D1. As shown in FIG. 6, in the first information D1, a type of lesion is "mass", a diameter is "maximum diameter 46 mm", definitive diagnosis of malignity is "primary lung cancer", a treatment content is "after gefitinib treatment", and a change in size is "increase". These labels are Nodule, Diameter, Malignant, Treated, and Progress, respectively.

In addition, the analysis result includes a segment of the lesion in the lung which is "upper left section", and a type of an absorption value which is a solid type, presence of a spicula, presence of calcification, absence of a cavity, and presence of a pleural contact. These labels are Segment, Solid, Spiculated+, Calcification+, Cavity−, and Pleural-Contact+, respectively.

The diagnostic information shown in FIG. 6 includes a definitive diagnosis of malignity of primary lung cancer. In this case, the change in size of the lesion over time is more important than the analysis result of internal properties such as the presence of a spicula. For this reason, the learning model 23A is constructed so as to generate a finding sentence to include only a change in size over time and not to include an analysis result indicating internal properties, or generate a finding sentence not to include an analysis result inconsistent with a definitive diagnosis (for example, a finding suggesting benignity in a case where there is a definitive diagnosis of primary lung cancer).

For example, the learning model 23A is constructed by training the recurrent neural network using training data including the labels of the diagnostic information and the analysis result shown in FIG. 6 and a training sentence "[Malignant] of [Segment] is [Treated]. [Nodule] is further increased in [Diameter]". In the constructed learning model 23A, in a case where the diagnostic information and the analysis result are input, the analysis result is selected based on the diagnostic information and the finding sentence is generated. Specifically, the learning model 23A is constructed by training performed such that in a case where the diagnostic information and the analysis result shown in FIG. 6 are input, a finding sentence "[Malignant] of [Segment] is [Treated]. [Nodule] is further increased in [Diameter]" is output. The sentence generation unit 23 embeds the diagnostic information and the analysis result into the label of the finding sentence output from the learning model 23A to generate a finding sentence "The primary lung cancer in the upper left section is in a condition after gefitinib treatment. A mass is further increased to a maximum diameter of 46 mm".

In order to reduce the certainty factor for the analysis result in the finding sentence described in the second information D2, the third information D3, and the fourth information D4, a finding sentence described in a non-assertive expression may be generated. Conversely, in order to increase the certainty factor for the analysis result, a finding sentence described in an assertive expression may be generated. The non-assertive expression is, for example, "~ is suspected", and the assertive expression is, for example, "~ is recognized". As described above, in the generated finding sentence, in order to decrease or increase the certainty factor for the analysis result, the learning model 23A may be constructed by training the recurrent neural network 40 using a training sentence in which the certainty factor for the analysis result is increased or a training sentence in which the certainty factor for the analysis result is decreased, according to the diagnostic information.

For example, as shown in FIG. 7, it is assumed that the labels of the diagnostic information are Nodule [MASS] and Diameter [MAJOR AXIS 48 mm], and the labels of the analysis result are Segment [LOWER RIGHT LOBE S6], Solid [SOLID TYPE], IrregularForm [IRREGULAR FORM], Spiculated+ [PRESENCE OF SPICULA], Lobulated+ [PRESENCE OF LOBULATED SHAPE], Airbronchogram+ [PRESENCE OF AIR BRONCHOGRAM], Cavity+ [PRESENCE OF CAVITY], Calcification– [ABSENCE OF CALCIFICATION], and PleuralContact+ [PRESENCE OF PLEURAL CONTACT]. The content in parentheses represents a specific content of each label. In this case, the finding sentence generated by the sentence generation unit 23 is "An irregular solid mass having a major axis of 48 mm in contact with the pleura is recognized in the lower right lobe S6. The mass is lobulated and accompanied by a spicula. An air bronchogram and a cavity are recognized inside. The calcification is not recognized". In the generated finding sentence, for a property item whose presence or absence is clear, the sentence ends with "~ is recognized", "~ is not recognized", or "~ is accompanied by ~".

On the other hand, as shown in FIG. 8, it is assumed that the labels of the diagnostic information are Nodule [MASS] and Diameter [MAJOR AXIS 48 mm], and the labels of the analysis result are Segment [LOWER RIGHT LOBE S6], Solid [SOLID TYPE], IrregularForm [IRREGULAR FORM], Spiculated+ [PRESENCE OF SPICULA], Lobulated+[PRESENCE OF LOBULATED SHAPE], Airbronchogram? [AIR BRONCHOGRAM UNCLEAR], Cavity? [CAVITY UNCLEAR], Calcification– [ABSENCE OF CALCIFICATION], and PleuralContact+[PRESENCE OF PLEURAL CONTACT]. The property item to which "?" is attached represents a false-positive analysis result.

In this case, the finding sentence generated by the sentence generation unit 23 is "An irregular solid mass having a major axis of 48 mm in contact with the pleura is recognized in the lower right lobe S6. The mass is lobulated and accompanied by a spicula. A low absorption area is recognized and an air bronchogram and a cavity are suspected inside. The calcification is not recognized". In the generated finding sentence, for a property item whose presence or absence is clear, the sentence ends with "~ is recognized", "~ is not recognized", or "~ is accompanied by ~". However, for a property whose presence or absence is unclear, that is, a false-positive property item, the sentence ends with "~ is suspected".

In order to change the certainty factor of the sentence generated in this way, the 1-hot expressions of "Airbronchogram? [AIR BRONCHOGRAM UNCLEAR]" and "Cavity? [CAVITY UNCLEAR]" are defined in advance, the learning model 23A is constructed by training the neural network using training data that includes the labels of "Airbronchogram? [AIR BRONCHOGRAM UNCLEAR]" and "Cavity? [CAVITY UNCLEAR]" and includes a training sentence that ends with "~ is suspected", whereby it is possible to generate a finding sentence with a certainty factor different according to the label.

In addition, by adding an expression according to the certainty factor, that is, an expression vector of "suspected" to the vector representation $x_t$ of the air bronchogram and the cavity input to the decoder 42 shown in FIG. 5, it is possible to generate a finding sentence that ends with "suspected". Alternatively, it is also possible to generate a finding sentence that ends with "suspected" by deriving a vector representation in which a component corresponding to 1 in the 1-hot expressions of "air bronchogram" and "cavity" is changed according to the certainty factor. In this case, for example, in a case where the 1-hot expression of "air bronchogram" is (1,0,0), the 1-hot expression may be changed to (0.5,0,0) in accordance with the certainty factor.

As a result, the learning model 23A is constructed which generates a sentence that ends with a high certainty factor for a property item whose presence or absence is clear, but generates a sentence that ends with a low certainty factor for a property item whose presence or absence is unclear.

On the other hand, regarding the importance, an order according to the importance is given to each item included in the diagnostic information and the analysis result. In the present embodiment, it is assumed that a table defining the importance for each item of the diagnostic information and the analysis result is stored in the storage 13. The sentence generation unit 23 gives an order according to the importance for each item of the diagnostic information and the analysis result with reference to the table stored in the storage 13. Then, the learning model 23A is constructed by training the recurrent neural network 40 such that the importance is changed according to whether the property is negative or positive and further according to the diagnostic information and a finding sentence including a predetermined number of analysis results is generated in order of the importance.

For example, the calcification is generally a benign property. Further, a negative property has less importance than a positive property item. For this reason, the learning model 23A is constructed such that the importance of calcification and negative property items included in the analysis result is decreased, the importance of positive property items is increased, and a finding sentence is generated using a predetermined number of property items having high importance. Depending on the confirmed diagnosis result included in the diagnostic information, it may be better to describe a negative property item for a specific property item in the finding sentence. In this case, the learning model 23A is constructed such that a finding sentence is generated with high importance even in a case where a specific property is negative according to the diagnostic information.

For example, as shown in FIG. 9, it is assumed that the labels of the diagnostic information are Nodule [MASS] and Diameter [MAJOR AXIS 24 mm], and the labels of the analysis result are Segment [LOWER RIGHT LOBE S6], Solid [SOLID TYPE], Lobulated+ [PRESENCE OF LOBULATED SHAPE], Airbronchogram– [ABSENCE OF AIR BRONCHOGRAM], Cavity– [ABSENCE OF CAVITY], Calcification– [ABSENCE OF CALCIFICATION], and PleuralContact+ [PRESENCE OF PLEURAL CONTACT]. Further, as shown in FIG. 9, it is assumed that numbers are given to respective items of the diagnostic information and the analysis result in order of the importance. In the present embodiment, it is assumed that the learning model 23A is constructed so as to include high-order n (for example, five) labels having high importance for the diagnostic information and the analysis result.

In this case, as shown in FIG. 9, in a case where the diagnostic information and the analysis result to which the importance is given are input to the learning model 23A, a finding sentence "[Nodule] of [Lobulated+] with [Pleural-Contact+] [Diameter] is recognized in [Segment]" is output. The sentence generation unit 23 embeds the diagnostic information and the analysis result into the label included in the finding sentence output from the learning model 23A to generate a finding sentence "A lobulated nodule having a major axis of 24 mm in contact with the pleura is recognized in the lower right lobe S6".

As shown in FIG. 10, in addition to the diagnostic information and the analysis result shown in FIG. 9, it is assumed that HistoryOsteosarcoma (PRESENCE OF OSTEOSARCOMA HISTORY) is added as a history of the first information D1 to the diagnostic information. In a case where there is a history of osteosarcoma, benign-like calcifications may be formed. For this reason, in a case where there is a history of osteosarcoma, it is necessary to ensure that a doctor confirms recurrence and metastasis of osteosarcoma included in the medical image G0 at the time of reading the finding sentence. Therefore, in a case where the history of osteosarcoma is included in the diagnostic information, the learning model 23A is constructed such that a finding sentence is generated by increasing the importance of the label of "absence of calcification". As a result, for example, in the learning model 23A, the finding sentence is generated such that the importance of "absence of calcification" is changed to 4, and the importance of the property items whose importance is 4 to 8 in FIG. 9 is changed to 5 to 9. As a result, the finding sentence generated by the sentence generation unit 23 is "A lobulated nodule having a major axis of 24 mm is recognized in the lower right lobe S6. The osteosarcoma is recognized. The calcification is not recognized". The learning model 23A may be constructed such that the finding sentence includes information indicating that there is a history of osteosarcoma.

The display control unit 24 displays the medical sentence generated by the sentence generation unit 23 on the display 14.

Next, a process performed in the first embodiment will be described. FIG. 11 is a flowchart showing the process performed in the first embodiment. In a case where an instruction to start the process is issued, the information acquisition unit 21 acquires the medical image G0 for which a finding sentence is to be generated and the diagnostic information (step ST1). Next, the analysis unit 22 analyzes the medical image G0 to derive the analysis result of the medical image G0 (step ST2). Then, the sentence generation unit 23 generates a finding sentence related to a patient as a medical sentence based on the analysis result derived by the analysis unit 22 and the diagnostic information (step ST3). Further, the display control unit 24 displays the medical sentence on the display 14 (step ST4), and the process ends.

As described above, in the present embodiment, the medical sentence related to the patient is generated based on the analysis result and the diagnostic information. Therefore, the generated medical sentence reflects not only the analysis result but also the diagnostic information on the patient. Therefore, according to the present embodiment, it is possible to generate a sentence having a content accurately representing the status of the patient.

In addition, by generating the medical sentence including the analysis result selected based on the diagnostic information, it is possible to generate the medical sentence including a necessary analysis result according to the diagnosis result and not including an unnecessary analysis result.

Further, by generating the medical sentence including the analysis result with a priority corresponding to the diagnostic information, it is possible to generate the medical sentence in which the analysis result is described with a priority reflecting the diagnostic information.

By generating the medical sentence including the analysis result and the diagnostic information, it is possible to generate a medical sentence capable of referring to both the analysis result and the diagnostic information.

Figure 12:
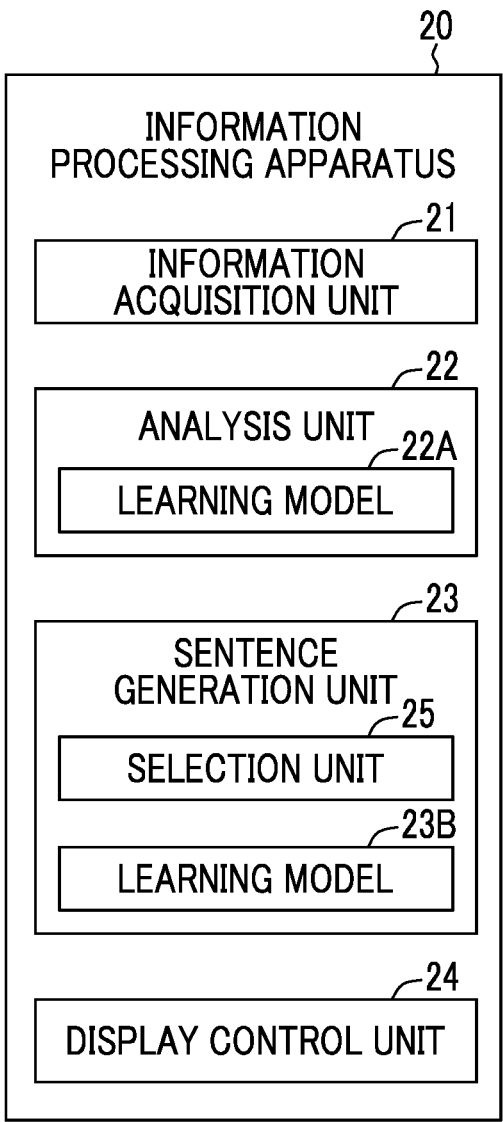
FIG. 12 is a block diagram showing an example of a functional configuration of an information processing apparatus according to a second embodiment.

In the above-described embodiment, the medical sentence is generated by inputting the diagnostic information and the analysis result to the learning model 23A of the sentence generation unit 23, but the present disclosure is not limited thereto. In the sentence generation unit 23, the analysis result may be selected according to the diagnostic information, and the medical sentence may be generated using the selected analysis result. Hereinafter, this configuration will be described as a second embodiment. FIG. 12 is a diagram showing a functional configuration of an information processing apparatus according to the second embodiment. In FIG. 12, the same components as those in FIG. 3 are denoted by the same references, and the detailed description thereof will not be repeated. As shown in FIG. 12, the information processing apparatus according to the second embodiment differs from the above-described embodiment in that the sentence generation unit 23 includes a selection unit 25 and a learning model 23B.

The selection unit 25 selects the analysis result derived by the analysis unit 22 based on the diagnostic information. For this reason, in the second embodiment, the storage 13 stores a table in which a rule for selecting an analysis result according to the diagnostic information is defined. FIG. 13 is a diagram showing an example of the table in which the rule is defined. As shown in FIG. 13, a table T1 defines each item of the analysis result in a horizontal direction and each item included in the diagnostic information in a vertical direction, and defines selection of whether or not to input each item of the diagnostic information and the analysis result to the learning model 23B. In the table T1, with respect to the diagnostic information, x is given to the item of the analysis result which is not selected and o is given to the item which is selected.

In the table T1, as the analysis result, an absorption value (solid type and frosted glass type), an edge (presence or absence of a spicula), an internal property (presence or absence of calcification, presence or absence of a cavity), and a periphery (presence or absence of a pleural invagination) are defined. In the second embodiment, similarly to FIG. 5, a segment, a diameter, definitive diagnosis of malignity, a treatment content, and a change in size are used as the diagnostic information. However, only the diameter and the definitive diagnosis of malignity are defined in the column of the table T1 for simplicity of description. Further, the diameter is classified into less than 5 mm (<5 mm) and 5 mm or more and less than 10 mm (<10 mm).

In the table T1, for a small abnormal shadow, in a case where the slice interval of the CT image is 5 mm, it is difficult to check a fine structure due to a partial volume effect. Therefore, among the absorption value, the edge, and the internal property included in the analysis result, items of the presence or absence of a cavity and the periphery are removed from the analysis result. Since the calcification is noticeable with high brightness in the image, the item of presence of calcification is left in the analysis result. In addition, in a case where the diameter is equal to or greater than 5 mm and less than 10 mm, since it is difficult to confirm the internal property of the abnormal shadow, the negative internal property is removed from the analysis result. However, both positive and negative for the calcification among the internal properties are left in the analysis result. In addition, in a case where the definitive diagnosis of malignity is included, the change in size of the lesion over time is more important than the analysis result of the internal property such as the presence of the spicula. For this reason, items of the absorption value, the edge, the internal property, and the periphery are removed from the analysis result.

In the table T1, in a case where the diameter and the definitive diagnosis of malignity overlap in determination of whether or not to be left in the analysis result, the analysis result is selected with priority given to deletion from the analysis result. Therefore, in a case where the diameter is equal to or greater than 5 mm and less than 10 mm and the definitive diagnosis of malignity is included in the diagnostic information, the selection unit 25 selects the analysis result substantially according to the definitive diagnosis of malignity by referring to the table T1.

The learning model 23B in the second embodiment is constructed by training a neural network such as a recurrent neural network in the same manner as the learning model 23A using training data in which combinations of various analysis results after being selected and various types of diagnostic information are associated with a training sentence to be generated from the analysis results and the diagnostic information. The learning model 23A in the first embodiment selects the input analysis result to generate the finding sentence. However, in the second embodiment, the analysis result to be input to the learning model 23B has already been selected. Therefore, the learning model 23B generates the finding sentence using the input analysis result and diagnostic information.

For example, in the second embodiment, in a case where the information acquisition unit 21 acquires the diagnostic information and the analysis result shown in FIG. 5, the selection unit 25 selects the analysis result with reference to the table T1. Since the diagnostic information shown in FIG. 5 includes the definitive diagnosis of malignity, the selection unit 25 removes items of the absorption value, the edge, the internal property, and the periphery from the analysis result, and inputs the diagnostic information and the selected analysis result to the learning model 23B. Specifically, the selection unit 25 inputs Nodule which is a label of a mass, Diameter which is a label of a maximum diameter 46 mm, Segment which is a label of an upper left section, Malignant which is a label of primary lung cancer, Treated which is a label after gefitinib treatment, and Progress which is a label of increase to the learning model 23B. The learning model 23B outputs a finding sentence "[Malignant] in [Segment] is [Treated]. [Nodule] is further increased in [Diameter]." The sentence generation unit 23 embeds the diagnostic information and the analysis result into the label included in the finding sentence output from the learning model 23A to generate a finding sentence "The primary lung cancer in the upper left section is in a condition after gefitinib treatment. A mass is further increased to a maximum diameter of 46 mm".

In the second embodiment, the analysis result of the analysis unit 22 may be a property score itself for each property item. In this case, the selection unit 25 determines whether the property item is positive or negative by comparing the property score with a threshold value, but the threshold value may be changed according to the diagnostic information. For example, in a case where the diagnostic information and the analysis result are as shown in FIG. 10, a threshold value for determining the calcification is decreased to determine that the calcification is present. In this case, in a case where the table T1 is derived such that the presence of calcification is left in the analysis result, a finding sentence including the content of the presence of calcification is generated in case where there is a history of osteosarcoma. For this reason, a radiologist who views a finding sentence performs interpretation of a medical image with an emphasis on the calcification.

In each of the above-described embodiments, the technology of the present disclosure is applied to a case of generating a finding sentence to be described in an interpretation report as a medical document, but the present disclosure is not limited thereto. For example, the technology of the present disclosure may be applied to a case of creating medical documents other than an interpretation report, such as an electronic medical record and a diagnostic report, and other documents including character strings related to images.

In each of the above-described embodiments, various processes are performed using the medical image G0 in which the diagnosis target is the lung, but the diagnosis target is not limited to the lung. In addition to the lung, any part of the human body such as the heart, liver, brain, and limbs can be the diagnosis target.

Further, in each of the above-described embodiments, the processing of the analysis unit 22 in the information processing apparatus 20 included in the interpretation WS 3 may be performed, for example, by an external device such as another analysis server connected to the network 10. In this case, the external device acquires the medical image G0 from the image server 5 and derives the analysis result by analyzing the medical image G0. Then, the information processing apparatus 20 generates a finding sentence using the analysis result derived by the external device.

In the above-described embodiment, for example, the following various processors can be used as a hardware structure of processing units performing various processes, such as the information acquisition unit 21, the analysis unit 22, the sentence generation unit 23, the display control unit 24, and the selection unit 25. As described above, in addition to the CPU which is a general-purpose processor executing software (program) to function as various processing units, the various processors include a programmable logic device (PLD) which is a processor capable of changing a circuit configuration after manufacture such as a field programmable gate array (FPGA), a dedicated electric circuit which is a processor having a circuit configuration exclusively designed to execute specific processing such as an application specific integrated circuit (ASIC), and the like.

One processing unit may be configured by one of the various processors, or may be configured by a combination of two or more processors of the same type or different types (for example, a combination of a plurality of FPGAs or a combination of a CPU and an FPGA). In addition, a plurality of processing units may be configured by one processor. As an example in which the plurality of processing units are configured by one processor, first, as typified by a computer such as a client or a server, there is a form in which one processor is configured by a combination of one or more CPUs and software and this processor functions as the plurality of processing units. Second, as typified by a system on chip (SoC) or the like, there is a form in which a processor that realizes functions of an entire system including a plurality of processing units with one integrated circuit (IC) chip is used. As described above, the various processing units are configured using one or more of the various processors as a hardware structure.

Furthermore, as the hardware structure of the various processors, more specifically, an electric circuit (circuitry) in which circuit elements such as semiconductor elements are combined can be used.

What is claimed is:

1. An information processing apparatus comprising at least one processor, wherein the processor is configured to:

acquire one or more analysis results related to a medical image of a patient;

acquire diagnostic information related to a diagnosis of the patient other than the analysis results; and generate a medical sentence related to the patient based on the analysis results and the diagnostic information, wherein the processor is further configured to:

select the analysis result based on the diagnostic information; and generate a medical sentence including the selected analysis result, wherein the diagnostic information includes first information representing an examination result performed on the patient, wherein the first information includes at least one of an examination result of a diagnostic apparatus different from an imaging apparatus that acquires the medical image of the patient, an analysis result of a medical image of a type different from the medical image, or an examination result of biological information of the patient.

2. The information processing apparatus according to claim 1, wherein the processor is configured to generate the medical sentence including the analysis result with a priority corresponding to the diagnostic information.

3. The information processing apparatus according to claim 1, wherein the processor is configured to generate the medical sentence including the diagnostic information and the analysis result.

4. The information processing apparatus according to claim 1, wherein the diagnostic information includes second information confirmed for a lesion included in the medical image.

5. The information processing apparatus according to claim 4, wherein the second information includes at least one of a measurement result of the lesion, a definitive diagnosis result for the lesion, or a history of the patient.

6. The information processing apparatus according to claim 1, wherein the diagnostic information includes confirmed third information other than information related to a lesion included in the medical image.

7. The information processing apparatus according to claim 6, wherein the third information includes at least one of a purpose of an examination in which the medical image is acquired or an image condition related to the medical image.

8. The information processing apparatus according to claim 1, wherein the diagnostic information includes fourth information representing a determination result for the medical image by a radiologist.

9. The information processing apparatus according to claim 8, wherein the fourth information includes at least one of an unconfirmed diagnosis result related to the medical image, a relevance between a lesion included in the medical image and a tissue other than the lesion, or a selection result of the analysis result by the radiologist.

10. An information processing method comprising:

acquiring one or more analysis results related to a medical image of a patient;

acquiring diagnostic information related to a diagnosis of the patient other than the analysis results;

generating a medical sentence related to the patient based on the analysis results and the diagnostic information;

selecting the analysis result based on the diagnostic information; and generating a medical sentence including the selected analysis result, wherein the diagnostic information includes first information representing an examination result performed on the patient, wherein the first information includes at least one of an examination result of a diagnostic apparatus different from an imaging apparatus that acquires the medical image of the patient, an analysis result of a medical image of a type different from the medical image, or an examination result of biological information of the patient.

11. A non-transitory computer-readable storage medium that stores an information processing program causing a computer to execute:

a step of acquiring one or more analysis results related to a medical image of a patient;

a step of acquiring diagnostic information related to a diagnosis of the patient other than the analysis results;

a step of generating a medical sentence related to the patient based on the analysis results and the diagnostic information;

a step of selecting the analysis result based on the diagnostic information; and a step of generating a medical sentence including the selected analysis result, wherein the diagnostic information includes first information representing an examination result performed on the patient, wherein the first information includes at least one of an examination result of a diagnostic apparatus different from an imaging apparatus that acquires the medical image of the patient, an analysis result of a medical image of a type different from the medical image, or an examination result of biological information of the patient.

* * * * *